US009516259B2

(12) United States Patent
Zheng

(10) Patent No.: US 9,516,259 B2
(45) Date of Patent: Dec. 6, 2016

(54) CAPTURING MEDIA CONTENT IN ACCORDANCE WITH A VIEWER EXPRESSION

(71) Applicant: Google Inc., Mountain View, CA (US)

(72) Inventor: Ying Zheng, Mountain View, CA (US)

(73) Assignee: GOOGLE INC., Mountain View, CA (US)

( * ) Notice: Subject to any disclaimer, the term of this patent is extended or adjusted under 35 U.S.C. 154(b) by 0 days.

(21) Appl. No.: 14/060,515

(22) Filed: Oct. 22, 2013

(65) Prior Publication Data

US 2015/0110471 A1 Apr. 23, 2015

(51) Int. Cl.
H04N 9/80 (2006.01)
H04N 5/775 (2006.01)
(Continued)

(52) U.S. Cl.
CPC .............. H04N 5/76 (2013.01); A61B 5/0022 (2013.01); A61B 5/0077 (2013.01); A61B 5/165 (2013.01); G02B 7/34 (2013.01); G02B 27/0093 (2013.01); G02B 27/017 (2013.01); G02B 27/34 (2013.01); G06F 3/011 (2013.01); G06F 3/017 (2013.01); G06K 9/00302 (2013.01); H04N 1/00336 (2013.01); H04N 5/23219 (2013.01); A61B 2503/12 (2013.01); G02B 2027/0187 (2013.01); G06F 2203/011 (2013.01)

(58) Field of Classification Search
USPC ......................................... 386/230–231, 248
See application file for complete search history.

(56) References Cited

U.S. PATENT DOCUMENTS 7,466,898 B2 * 12/2008 Ohashi ................... H04N 7/163
386/241
7,650,057 B2 * 1/2010 Takeshita ................. H04N 5/76
386/248
(Continued)

FOREIGN PATENT DOCUMENTS

EP 2402839 A2 1/2012
WO WO 2013/022156 2/2013

OTHER PUBLICATIONS

Google Inc., International Search Report and Written Opinion, PCT/US2014/061803, Feb. 16, 2015, 10 pgs.
(Continued)

Primary Examiner — Nigar Chowdhury
(74) Attorney, Agent, or Firm — Morgan, Lewis & Bockius LLP

(57) ABSTRACT

Systems and methods for capturing media content in accordance with viewer expression are disclosed. In some implementations, a method includes: at a computer system having one or more processors and memory storing one or more programs for execution by the one or more processors: detecting display of a media content item; while the media content item is being displayed: detecting a viewer expression corresponding to a predefined viewer expression; and in response to detecting the viewer expression: identifying a portion of the media content item corresponding in time to the viewer expression. In some implementations, the viewer expression—selected from one of: a facial expression, a body movement, a voice, or an arm, leg or finger gesture—is presumed to be a viewer reaction to the portion of the media content item.

21 Claims, 9 Drawing Sheets

(51) Int. Cl.

| | |
|---|---|
| *H04N 5/76* | (2006.01) |
| *G06F 3/01* | (2006.01) |
| *A61B 5/16* | (2006.01) |
| *H04N 1/00* | (2006.01) |
| *H04N 5/232* | (2006.01) |
| *G06K 9/00* | (2006.01) |
| *G02B 27/00* | (2006.01) |
| *A61B 5/00* | (2006.01) |
| *G02B 7/34* | (2006.01) |
| *G02B 27/34* | (2006.01) |
| *G02B 27/01* | (2006.01) |

(56) References Cited

U.S. PATENT DOCUMENTS

| | | |
|---|---|---|
| 2002/0032689 A1 | 3/2002 | Abbott, III et al. |
| 2014/0137144 A1* | 5/2014 | Jarvenpaa et al. ............... 725/13 |
| 2014/0244748 A1* | 8/2014 | Lintz ............................ 709/204 |

OTHER PUBLICATIONS

Google Inc., International Preliminary Report on Patentability, PCT/US2014/061803, Apr. 26, 2016, 7 pgs.

\* cited by examiner

CAPTURING MEDIA CONTENT IN ACCORDANCE WITH A VIEWER EXPRESSION

TECHNICAL FIELD

The disclosed implementations relate generally to capturing media content in accordance with a viewer expression.

BACKGROUND

There is current interest in identifying and capturing media content moments in which individual users are particularly interested. For example, a viewer might want to save memorable or classic moments from a movie he or she is watching and then share then via social media applications or bookmark those moments for future reference. Also, viewers sometimes would like to review snapshots of those moments that correspond to particular emotional responses. For example, a viewer might want to review/save media moments that the user found to be particularly tragic, inspirational, or funny.

Difficulties abound; however, in identifying and saving such moments as simultaneously capturing movie moments and the associated viewer reactions typically requires the moments to be rerun (since viewer reactions become available only after those movie moments are viewed). This need to rerun the media content can result in an interrupted viewing experience and the loss of spontaneity in viewer reactions (i.e., the viewer response to the rerun moment might not be the same as to the original moment).

The above identified difficulties are reduced or eliminated by the systems and methods disclosed herein.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the drawings.

SUMMARY

Figure 1A:
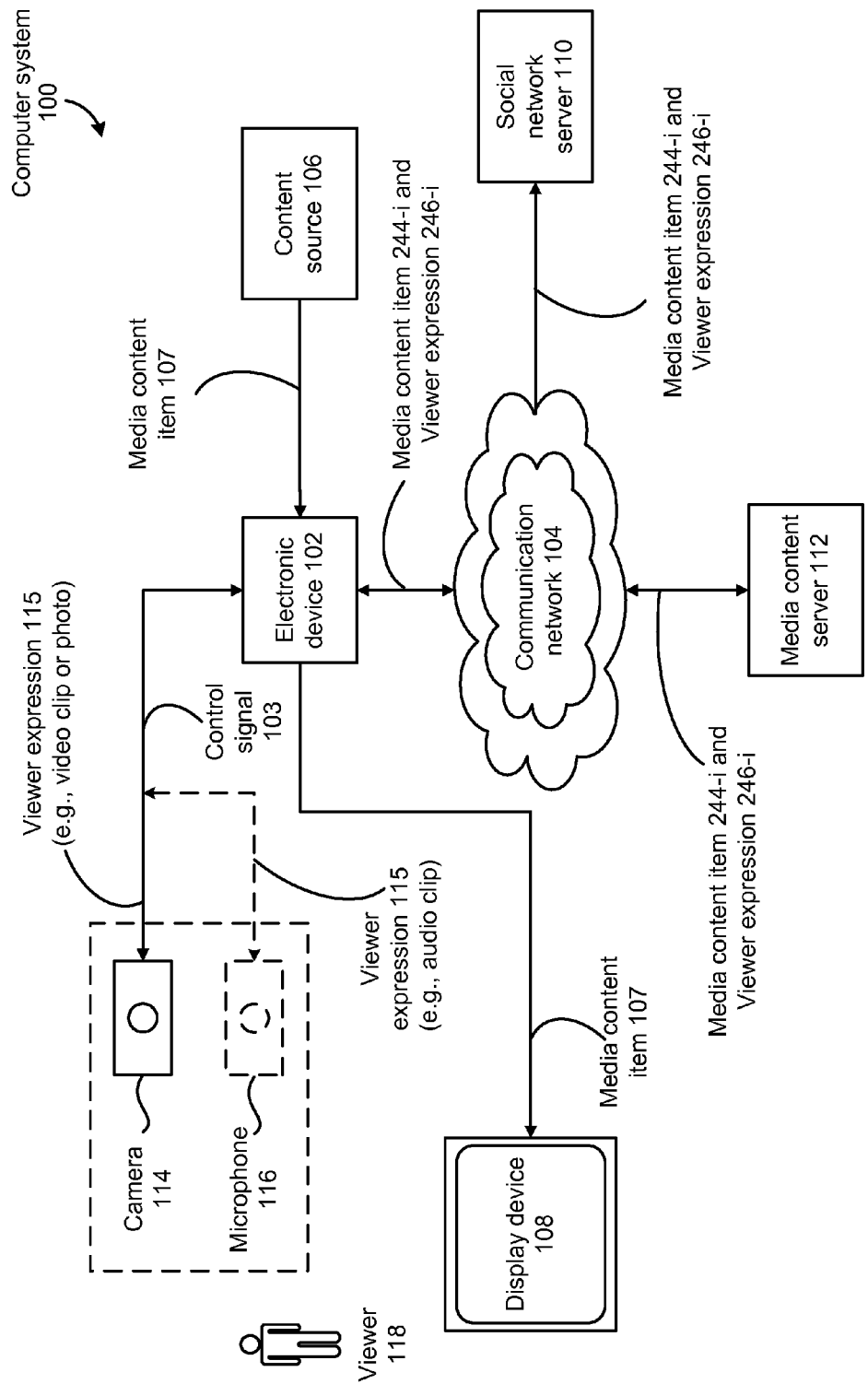
FIG. 1A is a block diagram illustrating a computer system, in accordance with some implementations.

Systems, methods, and computer readable storage mediums for capturing media content in accordance with a viewer expression are disclosed herein.

In one aspect of the present disclosure, a method for capturing media content in accordance with a viewer expression includes detecting display of a media content item and, while the media content item is being displayed, detecting a viewer expression corresponding to a predefined viewer expression. The method further includes, in response to detecting the viewer expression, identifying a portion of the media content item corresponding in time to the viewer expression. In some implementations, the method is executed at a computer system having one or more processors and memory storing one or more programs for execution by the one or more processors.

In some implementations, the viewer expression is presumed to be a viewer reaction to the portion of the media content item.

In some implementations, the method further comprises capturing (i) the viewer expression or (ii) a reference to the viewer expression, in a second media content item.

In some implementations, the method further comprises receiving a communication from a viewer identified in the viewer expression; and in response to receiving the communication: causing the second media content item to be shared with one or more other users.

In some implementations, the predefined viewer expression is selected from one of a facial expression, a body movement, a voice, or an arm, leg or finger gesture.

In some implementations, the portion of the media content is one of a video or audio clip, a text, or a photo.

In some implementations, the method further comprises uploading (i) the portion of the media content item or (ii) a reference to the portion of the media content item, to a server.

In some implementations, the method further comprises transmitting information identifying the viewer expression to a server.

In another aspect of the present disclosure, a system for capturing media content in accordance with a viewer expression includes one or more processors, memory, and one or more programs. The one or more programs are stored in the memory and are configured to be executed by the one or more processors. The one or more programs include instructions for detecting display of a media content item and, while the media content item is being displayed, detecting a viewer expression corresponding to a predefined viewer expression. The one or more programs also include instructions for, in response to detecting the viewer expression, identifying a portion of the media content item corresponding in time to the viewer expression.

In some implementations, the viewer expression is presumed to be a viewer reaction to the portion of the media content item.

In some implementations, the one or more programs further include instructions for: capturing (i) the viewer expression or (ii) a reference to the viewer expression, in a second media content item.

In some implementations, the one or more programs further include instructions for: receiving a communication from a viewer identified in the viewer expression; and in response to receiving the communication: causing the second media content item to be shared with one or more other users.

In some implementations, the predefined viewer expression is selected from one of: a facial expression, a body movement, a voice, or an arm, leg or finger gesture.

In some implementations, the portion of the media content is one of: a video or audio clip, a text, or a photo.

In some implementations, the one or more programs further include instructions for: uploading (i) the portion of the media content item or (ii) a reference to the portion of the media content item, to the server.

In some implementations, the one or more programs further include instructions for: transmitting information identifying the viewer expression to a server.

In another aspect of the present disclosure, a non-transitory computer readable storage medium for capturing media content in accordance with a viewer expression includes one or more programs having executable instructions. The instructions, when executed by a computer system with one or more processors, cause the computer system to detect display of a media content item and, while the media content item is being displayed. detect a viewer expression corresponding to a predefined viewer expression. The instructions also cause the computer system to, in response to detecting the viewer expression, identify a portion of the media content item corresponding in time to the viewer expression.

In some implementations, the viewer expression is presumed to be a viewer reaction to the portion of the media content item.

In some implementations, the one or more programs further include instructions to: capture (i) the viewer expression or (ii) a reference to the viewer expression, in a second media content item.

In some implementations, the one or more programs further include instructions to: receive a communication from a viewer identified in the viewer expression; and in response to receiving the communication: cause the second media content item to be shared with one or more other users.

In some implementations, the predefined viewer expression is selected from one of a facial expression, a body movement, a voice, or an arm, leg or finger gesture.

In some implementations, the portion of the media content is one of a video or audio clip, a text, or a photo.

In some implementations, the one or more programs further include instructions to: upload (i) the portion of the media content item or (ii) a reference to the portion of the media content item, to the server.

In some implementation, the one or more programs also include instructions to transmit information identifying the viewer expression to a server.

DETAILED DESCRIPTION

The implementations described herein provide techniques for capturing media content items or a portion thereof (e.g., snapshots or video clips) in accordance with a viewer's expressions. For example, in some implementations, after capturing (e.g., with a camera) an image of a viewer showing an identifiable emotion/expression, a set-top box or a connected TV automatically, and without intervention by the viewer—but with the viewer's prior consent—captures a short (e.g., 5-second) clip of the media content (e.g., movie or TV program) that the viewer was watching when the emotion was captured. For example, the captured expression might be one horror that occurred as the viewer was watching a horror film, such as Psycho. In some implementations, one or more captured expressions of the viewer are stored along with corresponding media content clips. Consequently, after finishing viewing the media item, the viewer can review both his/her reactions (e.g., a horrified face), and the associated movie clips (e.g., scary movie scenes) associated with that horrified expression. Similarly, without interrupting the viewing experience, viewers may review a portion of a recorded standup comedy performance, as well as photos or sound clips capturing them laughing, smiling, giggling, chuckling, or yawning while watching or listening to those portions of the standup comedy performance. Viewers can also share information about these TV/movie episodes as well as their reactions (e.g., laughing, horrified, or scared) with their friends. In some implementations, such sharing can be done using social media posts, text messages or email messages. Some implementations are configured to create such posts or messages based on user input and previous recordings of media clips and associated user expressions.

Because viewers are not required to take any extraneous actions to capture their expressions while viewing media content items (e.g., finding and positioning a camera and taking photos), the viewing experience is preserved and spontaneity in captured viewer expressions is preserved—as long as the viewers have provided their prior consent. More specifically, because viewer expressions are automatically captured as they occur, the captured viewer expressions are less likely to appear orchestrated or artificial. By requiring prior user consent, explicit or implicit, the viewer expression is captured and/or detected and then used for various social purposes, but only as authorized by the user, so as to protect user privacy and to comply with relevant privacy laws or contract provisions.

As a result, with a viewer's consent (e.g., by virtue of the user/viewer turning on a camera's an auto-capture mode or explicitly agreeing in advance to having their image captured and potentially made available for transmission to a server for possible sharing in a social media post, text or email message, etc.), viewer expressions and/or reactions are captured without sacrificing spontaneity.

Additional details of implementations are now described in relation to the Figures.

FIG. 1A is a block diagram illustrating a computer system 100, in accordance with some implementations.

In some implementations, the computer system 100 includes an electronic device 102 (e.g., a connected TV or a Google TV device), a communication network 104, a content source 106, a display device 108, a social network server 110, and a media content server 112. In some implementations, the electronic device 102 includes or is connected with: a camera 114 and optionally a microphone 116.

In some implementations, the electronic device 102 detects that a media content item (e.g., a movie, an MP3 song, or a document such as an email or a web page) is being displayed (e.g., on the display device 108). In some implementations, e.g., while a media content item is being displayed, the electronic device 102 detects a viewer expression corresponding to a predefined viewer expression For example, the electronic device 102 identifies a viewer expression as a smile by (i) capturing an image of a viewer's face (e.g., using the camera 114); and then (ii) comparing the captured facial impression to an image template (e.g., a predefined expression 240 in FIG. 2) that includes user expressions confirmed or verified as smiles, for similarities or lack thereof. In some implementations, the electronic device 102, responsive to detecting the viewer expression, identifies a portion of the media content item corresponding in time to the viewer expression. For example, after identifying a viewer as smiling or crying, the electronic device 102 captures an audio and/or video clip of a movie or TV episode that the viewer 118 was watching when the viewer laughed or cried.

In some implementations, detecting viewer expression requires more than a de minimis amount of processing time, and as such the electronic device 102 stores (or caches), in a temporary or permanent storage, a portion (e.g., past 30 seconds or past 2 minutes) of the media content item being displayed on the display device 108. In some implementations, after detecting a predefined viewer expression, the electronic device 102 retrieves the corresponding portion of the media content item previously cached in the temporary or permanent storage device.

In some implementations, the electronic device 102 includes or is communicably connected with a camera 114 and optionally a microphone 116. In some implementations, the camera 114 collects image, or audio or video clip of a viewer (e.g., viewer expressions 115), such as a smiley face, a raised arm or leg, and a viewer covering his/her eyes, nodding or shaking his/her head. In some implementations, the microphone 116 collects audio clips of a viewer (e.g., viewer expressions), such as a loud laugh, or an expressive verbal outburst, such as "GOODNESS!" "No!" or "Yes!" In some implementations, the electronic device 102 determines whether a viewer 118 is laughing, crying, or horrified, by comparing the captured image/video/audio clips (e.g., the predefined expressions 240 in FIG. 2) to saved clips known to include certain types of viewer expressions (e.g., a clip including chuckles, or an image having a shocked face).

In some implementations, the communication network 104 optionally includes the Internet, one or more local area networks (LANs), one or more wide area networks (WANs), other types of networks, or a combination of such networks.

In some implementations, the content source 106 provides one or more media content items (e.g., movies, TV episodes, emails, web pages, and photos) for display on the display device 108. In some implementations, the content source 106 is a TV broadcasting system, a cable TV provider, a satellite TV provider, a content purchasing/sharing/downloading service such as GOOGLE PLAY, or a network service provider such as an Internet service provider.

In some implementations, the display device 108 is a TV display, a computer display, an LED/LCD display, or a display wall.

In some implementations, the social network server 110 provides a viewer access to one or more social network applications, such as a GOOGLE+CIRCLE application, or a GOOGLE HANGOUT application. For example, when the electronic device 102 captures an image of a viewer crying after watching a documentary movie about natural disasters, a viewer 118 can share both the image and—with appropriate copyright permissions—a portion of the document movie, with his/her GOOGLE+CIRCLE friends, or upload the image and the movie portion (with appropriate copyright permissions) to a web blog, e.g., a blog at WORDPRESS.COM, for publication.

In some implementations, the media content server 112 enables a viewer to share viewer expressions and media content item, such as sharing audio/video clips on YOUTUBE.COM. For example, when the electronic device 102 captures a photo of a viewer cheering and hollering after watching, on live TV broadcast, a historic win by the home football team over a long time rival team, the viewer can (with appropriate copyright permissions) upload both the cheering and hollering photo and a portion of the live TV broadcast on YOUTUBE.COM or onto DROPBOX.COM, for sharing and/or for storage.

Figure 1B:
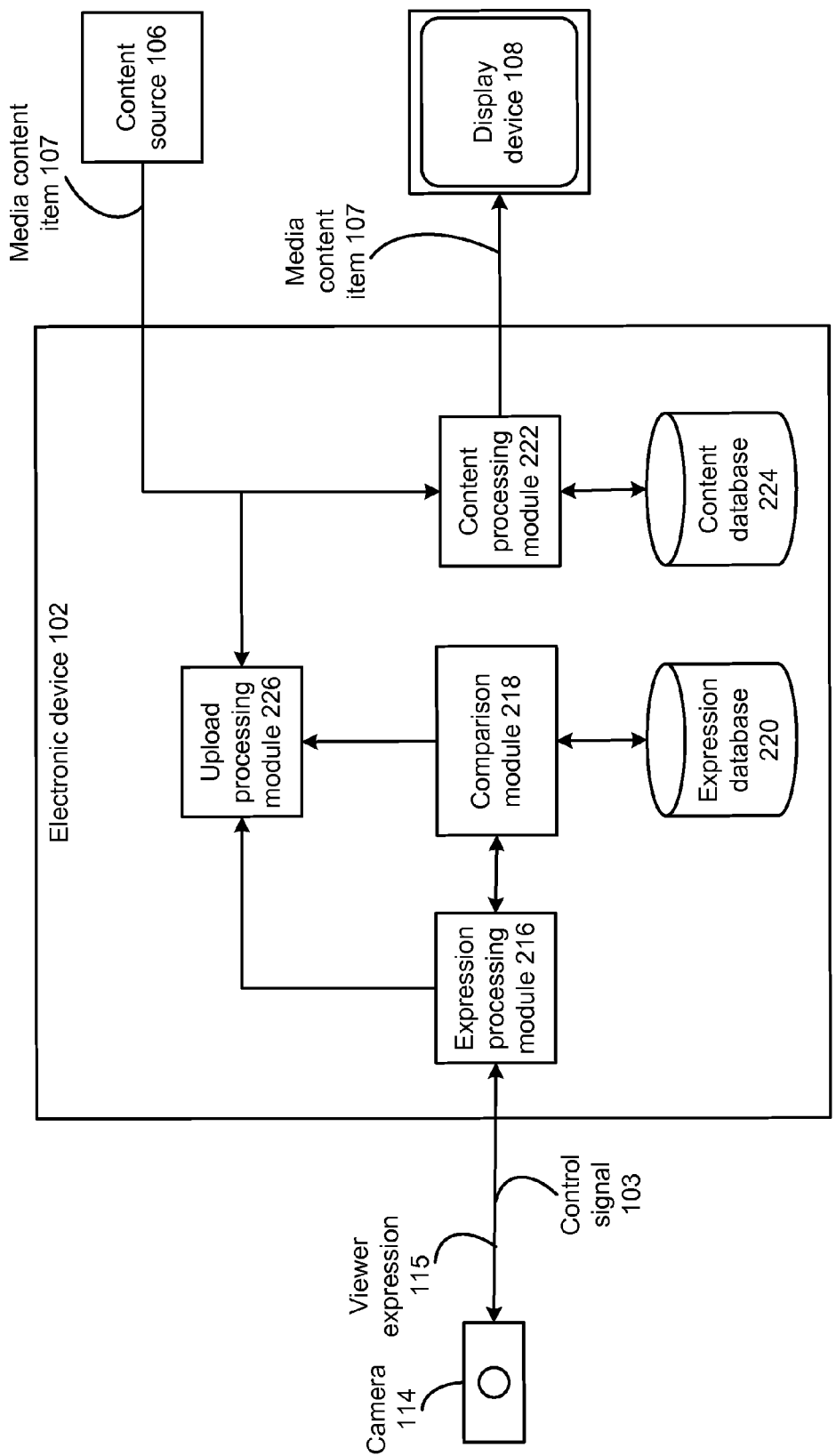
FIG. 1B is a block diagram illustrating an electronic device in accordance with some implementations.

FIG. 1B is a block diagram illustrating an electronic device 102, in accordance with some implementations.

In some implementations, the electronic device 102 includes an expression processing module 216, a comparison module 218, an expression database 220, a content processing module 222, and a content database 224.

In some implementations, the expression processing module 216 detects and captures viewer expressions, using the camera 114 and/or the microphone 116, and selectively stores captured viewer expressions in the expression database 220.

In some implementations, the comparison module 218 compares captured viewer expressions with viewer expression known or confirmed to include a particular type of view expression, e.g., a smiley-face photo, and an audio clip including a loud laugh or a series of chuckles. In some implementations, upon a determination that a captured viewer expression matches a particular type of known viewer expression (e.g., a smile, a cry, or shedding tears), the comparison module 218 determines (or identifies) what type of viewer expression was captured, e.g., a viewer is captured laughing, smiling, horrified, or shocked.

In some implementations, the upload processing module 226 uploads, upon a user request, a media content item (or a portion thereof) a viewer is consuming (e.g., watching or listening to), to either a social network server 110 (e.g., a GOOGLE+CIRCLE server) or a media content server 112 (e.g., a YOUTUBE.COM server).

In some implementations, the content processing module 222 prepares for display media content items received from the content source 106, on the display device 108. In some implementations, the content processing module 222 also stores captured viewer expressions and/or captured media content items, or a portion thereof, in the content database 224. In some implementations, the content processing module 222 cashes (or buffers) a portion of media content items a viewer has watched (e.g., last 10 second of a movie a viewer is watching) in the content database 224, so that the buffered media content item can be retrieve later on if necessary.

In some implementations, the content database 224 stores captured viewer expressions or corresponding media content items, for storage, for sharing and for uploading to the media content server 112 or to the social network server 110.

Figure 2:
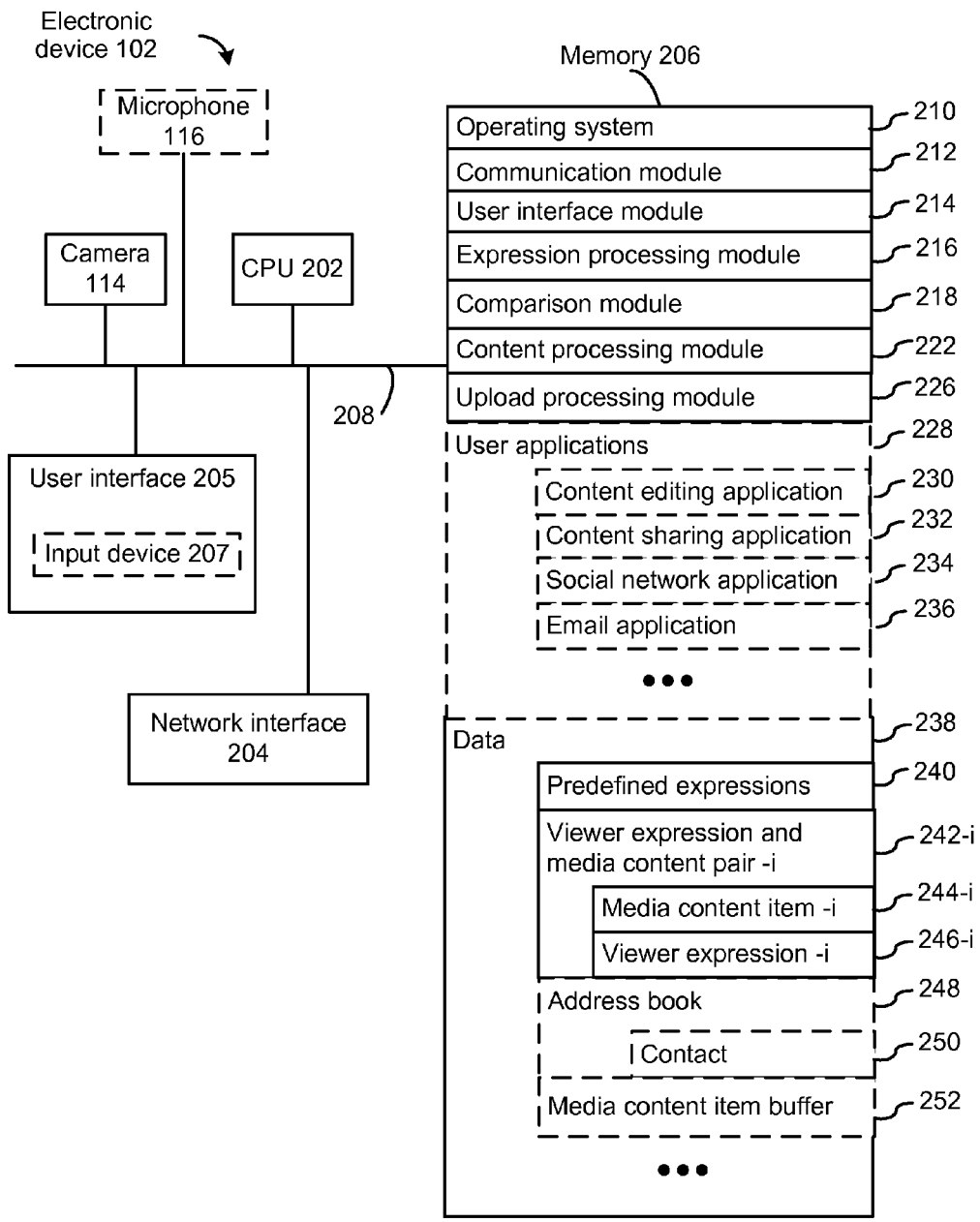
FIG. 2 is a block diagram illustrating an electronic device in accordance with some implementations.

FIG. 2 is a block diagram illustrating an electronic device 102, in accordance with some implementations. The electronic device 102 in some implementations includes one or more processing units CPU(s) 202 (also referred to as processors), one or more network interfaces 204, a viewer interface 205, a memory 206, and one or more communication buses 208 for interconnecting these components. The communication buses 208 optionally include circuitry (sometimes called a chipset) that interconnects and controls communications between system components. The memory 206 typically includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. The memory 206 optionally includes one or more storage devices remotely located from the CPU(s) 202. The memory 206, or alternatively the non-volatile memory device(s) within the memory 206, comprises a non-transitory computer readable storage medium. In some implementations, the memory 206 or alternatively the non-transitory computer readable storage medium stores the following programs, modules and data structures, or a subset thereof:
- an operating system 210, which includes procedures for handling various basic system services and for performing hardware dependent tasks;

a network communication module (or instructions) 212 for connecting the electronic device 102 with other devices (e.g., the content source 106 or the social network server 110) via one or more network interfaces 204 (wired or wireless), or the communication network 104 (FIG. 1);

a user interface module 214 for displaying user interface components or controls (e.g., textbox, button, radio button, drop-down list) to a user/viewer;

an expression processing module 216 for collecting and processing (e.g., image adjustment, such as facial recognition, cropping, and rotating) viewer expressions contained or captured in an image or an audio/video clip, or a portion thereof: e.g., identifying distinct expressions of two different viewers captured in the same photo;

a comparison module 218 for comparing captured viewer expressions with predefined expressions (e.g., comparing view expressions captured in an image with another image known or confirmed to include a smiling or a horrified face, comparing audio portion of a video clip with a sound clip confirmed to include a loud laugh or a series of giggles), and determines a category or type (e.g., smile, horrified, poise, or stone-face) to which the captured viewer expressions belong;

a content processing module 222 for preparing for display media content items received from the content source 106, on the display device 108;

an upload processing module 226 for preparing to upload viewer expressions captured, e.g., in an image, or in an audio/video clip, to a social network server or to a content media server, for sharing or for storage;

one of more user applications 228 for execution on the electronic device 102, which include:
  a content editing application 230 for editing a captured viewer expression (or a portion thereof) and/or a capture media content item (or a portion thereof);
  a content sharing application 232 for sharing a captured viewer expression (or a portion thereof) and/or a capture media content item (or a portion thereof) with one or more other users, such as a DROPBOX application, and a GOOGLE YOUTUBE application;
  a social network application 234 for providing a viewer access to one or more social networks, such as a GOOGLE+CIRCLE application; and
  an email application 236 for providing email access to a user for communicating with other users, such as a GOOGLE GMAIL application; and data 238 stored on the electronic device 102, which include:
  one or more predefined expressions 240, e.g., video frames and/or still photos known to describe/illustrate a set of expressions (such as a person crying or laughing), and/or associated sound clips or video frames confirmed to be associated with the same expressions; these predefined expressions 240 serve as templates for the purpose of comparison to captured user expressions;
  one or more viewer expression and media content pairs 242, each of which includes:
    a media content item 244-that includes media content, or a portion thereof, that was displayed on the display device 108 and then captured in association with a particular viewer expression 246-i. For example, a media content item might be 10 video frames and/or a 5 second sound clip of a TV episode that a viewer was watching on the display device 108; and
    a viewer expression 246-that corresponds in time to the media content item 244-and thus is presumed to be a viewer reaction to the media content item 244-i, e.g., a sound clip of a user laughing while watching a stand-up comedy show; note: the expression 246-might just be a description of the expression as compared to an actual captured sound clip or video frame showing the expression.
  an address book 248 (e.g., a GMAIL contact list), which includes:
    one or more user contacts 250, e.g., an email address, a cell phone number, a home address, and a work address; and
  a media content item buffer for storing media content item that has been displayed to a viewer in the past, e.g., within a predefined time period, such as 10 seconds or 5 seconds, from the current time.

In some implementations, the user interface 205 includes an input device 207 (e.g., a keyboard, a mouse, a touchpad, a track pad, and a touch screen) for a user to interact with the electronic device 102.

In some implementations, one or more of the above identified elements are stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 206 optionally stores a subset of the modules and data structures identified above. Furthermore, the memory 206 may store additional modules and data structures not described above.

Figure 3:
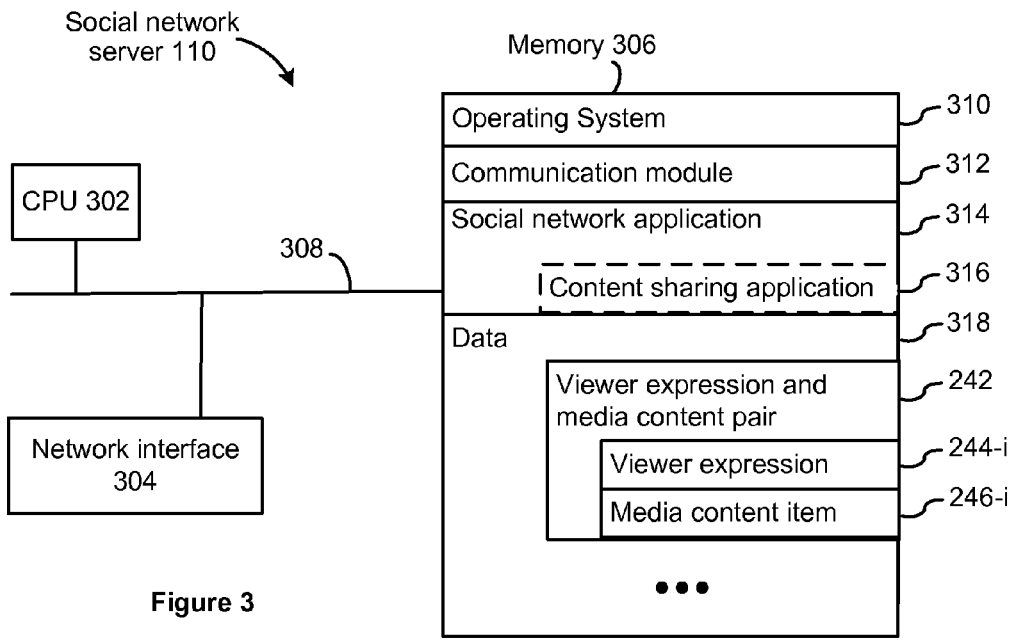
FIG. 3 is a block diagram illustrating a social network server in accordance with some implementations.

FIG. 3 is a block diagram illustrating a social network server 110, in accordance with some implementations. The social network server 110 typically includes one or more processing units CPU(s) 302 (also referred to as processors), one or more network interfaces 304, memory 306, and one or more communication buses 308 for interconnecting these components. The communication buses 308 optionally include circuitry (sometimes called a chipset) that interconnects and controls communications between system components. The memory 306 includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. The memory 306 optionally includes one or more storage devices remotely located from CPU(s) 302. The memory 306, or alternatively the non-volatile memory device(s) within the memory 306, comprises a non-transitory computer readable storage medium. In some implementations, the memory 306 or alternatively the non-transitory computer readable storage medium stores the following programs, modules and data structures, or a subset thereof:

an operating system 310, which includes procedures for handling various basic system services and for performing hardware dependent tasks;

a network communication module (or instructions) 312 for connecting the social network server 110 with other devices (e.g., the electronic device 102) via the one or more network interfaces 304 (wired or wireless), or the communication network 104 (FIG. 1);

one or more social network applications or other communication applications for enabling a user (e.g., a viewer of a media content item) to communicate with friends or contacts, e.g., a GOOGLE+CIRCLE application or a GMAIL application, which optionally include:

one or more content sharing applications for sharing media content item 244-(FIG. 2) and/or viewer expression (246-*i*) corresponding (e.g., in time) thereto, e.g., a GOOGLE DRIVE application; and data 318 stored on the social network server 110, which include:

one or more viewer expression and media content pairs 242, each of which includes:

a media content item 244-as described with reference to FIG. 2; and a viewer expression 246-as described with reference to FIG. 2.

Figure 4:
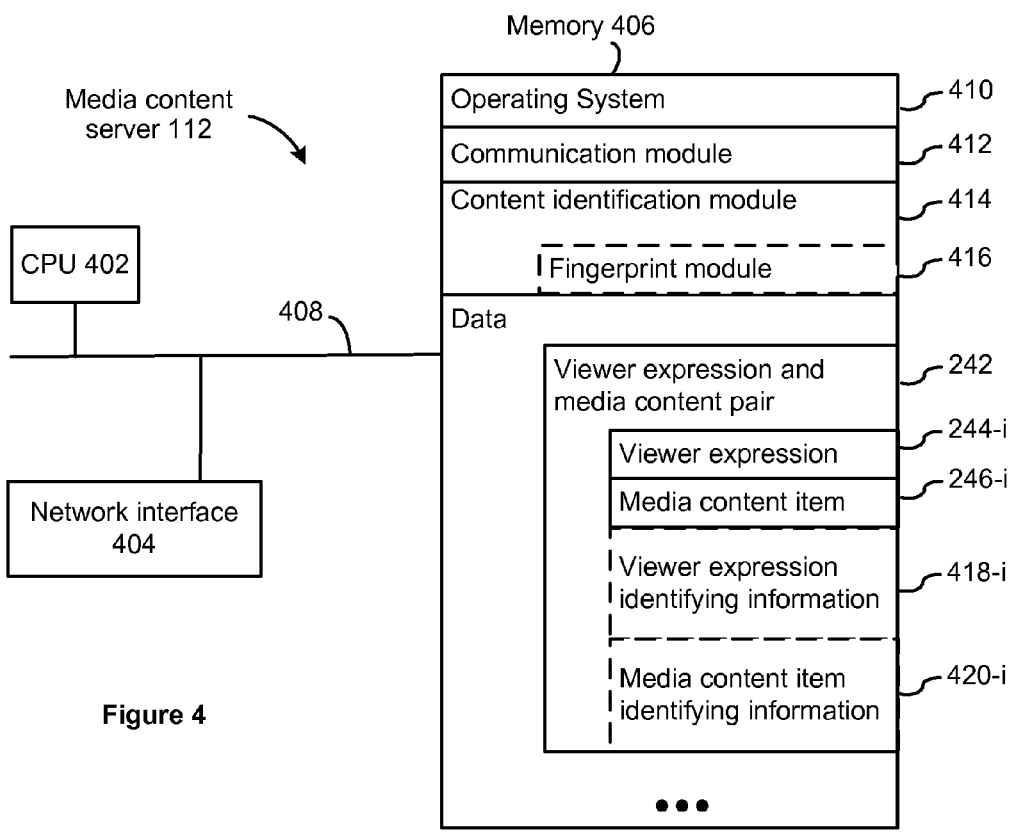
FIG. 4 is a block diagram illustrating a media content server in accordance with some implementations.

FIG. 4 is another block diagram illustrating a media content server 112, in accordance with some implementations. The media content server 112 typically includes one or more processing units CPU(s) 402 (also referred to as processors), one or more network interfaces 404, memory 406, and one or more communication buses 408 for interconnecting these components. The communication buses 408 optionally include circuitry (sometimes called a chipset) that interconnects and controls communications between system components. The memory 406 includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. The memory 406 optionally includes one or more storage devices remotely located from CPU(s) 402. The memory 406, or alternatively the non-volatile memory device(s) within the memory 406, comprises a non-transitory computer readable storage medium. In some implementations, the memory 406 or alternatively the non-transitory computer readable storage medium stores the following programs, modules and data structures, or a subset thereof:

an operating system 410, which includes procedures for handling various basic system services and for performing hardware dependent tasks;

a network communication module (or instructions) 412 for connecting the social network server 110 with other devices (e.g., the electronic device 102) via the one or more network interfaces 304 (wired or wireless), or the communication network 104 (FIG. 1);

a content identification module 414 for identifying media content items obtained from the electronic device 102 (e.g., an audio/video clip stored, temporarily or permanently on a Google TV device) or from the content source 106 (e.g., a TV episode being broadcasting over a cable TV network), which optionally includes:

a fingerprint module 416 for obtaining or generating content fingerprints (e.g., hash values) of a media content item, e.g., by applying a hash function to a video clip, or by sampling a portion of the video clip; and data 418 stored on the media content server 112, which include:

one or more viewer expression and media content pairs 242, each of which includes:

a media content item 244-as described with reference to FIG. 2; and a viewer expression 246-as described with reference to FIG. 2;

optionally, viewer expression identifying information 418-for uniquely identifying a viewer expression (e.g., a URL referencing a photo including a viewer's horrified face) or a file corresponding thereto (e.g., a JPEG file, Viewer1_HorrifiedFace_May_15_2012.jpg, showing a person's horrified face) stored on the social media server 112, on the electronic device 102, or on other computing devices; and optionally, media content item identifying information 420-for uniquely identifying a media content item (e.g., a URL referencing to a portion of a TV episode stored on the media content server 112) or a file corresponding thereto (e.g., a JPEG file, LawAndOrder_Episode1_May_15_2012.jpg, including a stored Law and Order episode) stored on the social media server 112, on the electronic device 102, or on other computing devices.

In some implementations, one or more of the above identified elements are stored in one or more of the previously mentioned memory devices, and corresponds to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 406 optionally stores a subset of the modules and data structures identified above. Furthermore, the memory 406 optionally stores additional modules and data structures not described above.

Although FIGS. 3 and 4 show a "social network server 110" and a "media content server 112," respectively, FIGS. 3 and 4 are intended more as functional description of the various features which may be present in server systems than as a structural schematic of the implementations described herein. In practice, and as recognized by those of ordinary skill in the art, items shown separately could be combined and some items could be separated.

Figure 5:
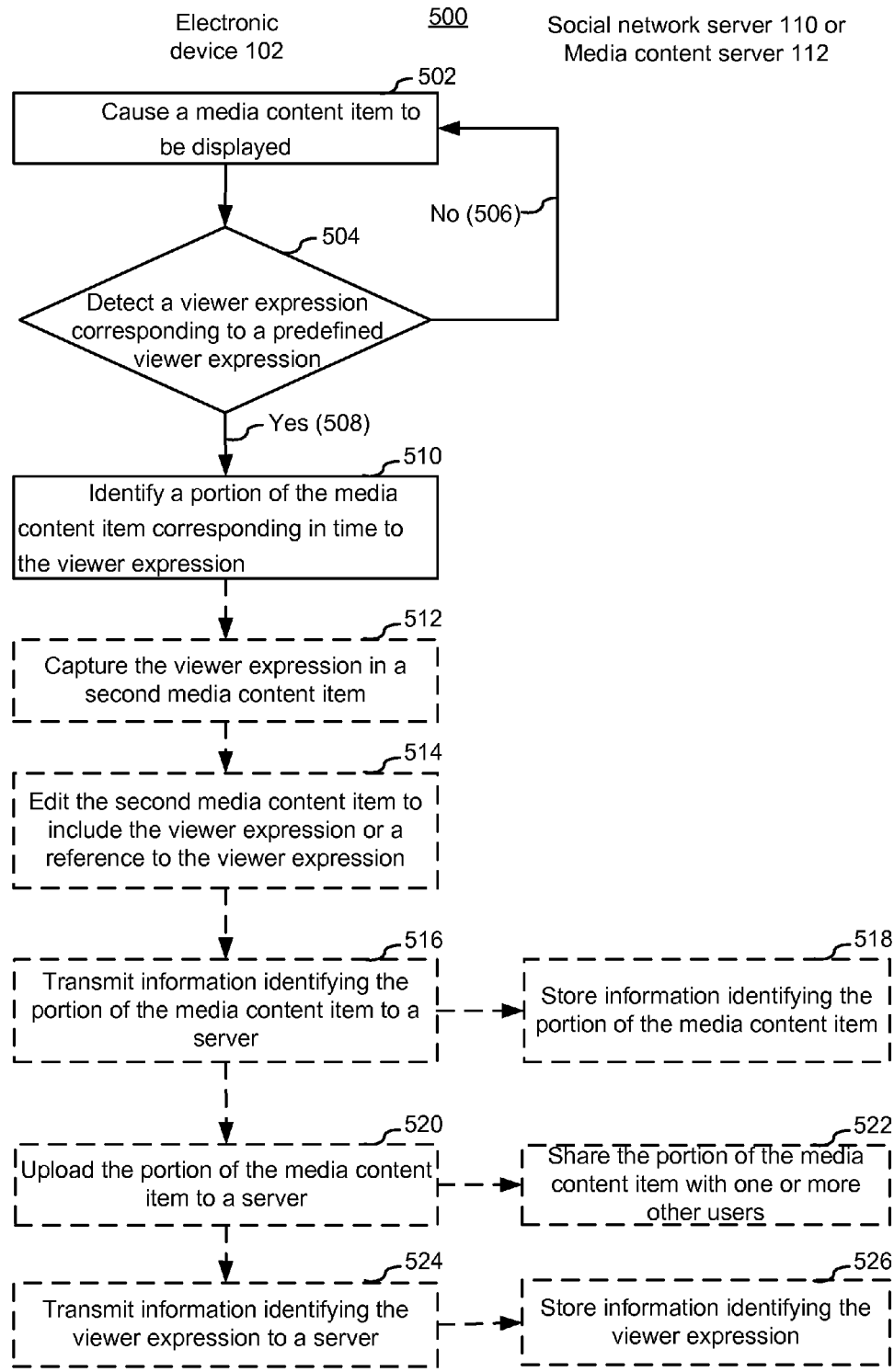
FIG. 5 is a flow chart illustrating a method for capturing media content in accordance with a viewer expression in a computer system in accordance with some implementations.

FIG. 5 is a flow chart illustrating a method 500 for capturing media content in accordance with viewer expression, e.g., implemented at electronic device 102, at the social network server 110, or at the media content server 112, in accordance with some implementations.

In some implementations, the electronic device 102 first causes (502) a media content item (e.g., a TV episode) to be displayed on the display device 108.

In some implementations, the electronic device 102 detects (504) whether a viewer expression corresponds to (e.g., matches) a predefined viewer expression. For example, a Google TV device or a set-top box detects whether a viewer expression captured (by a camera attached to the Google TV device) includes a viewer's laughing or smiling face. In some implementations, the detection includes: (A) using image comparison techniques to compare, for similarities or lack thereof, viewer expressions captured with an image or a video known or confirmed to include a particular category (or type) of viewer expression (e.g., a photo known to include a smiling face of a person); and (B) based on comparison results, determining what type of viewer expression is captured, e.g., a laughing face or a shocked face. In some implementations, the detection is carried out after a determination that a media content item is currently being displayed on the display device 108, to ensure that a captured viewer expression is presumably a reaction to watching/listing to the media content item, rather than to unrelated events (e.g., reading a magazine).

In some implementations, if the captured viewer expression does not ("No"; 506) correspond to (i.e., match) a predefined viewer expression, the electronic device 102 loops back to the step 502. In some implementations, the detection (504) is carried out again, on a random basis or according to a predefined time schedule (e.g., every 2 seconds or every other 400 milliseconds).

In some implementations, if the captured viewer expression does ("Yes"; 508) correspond to (i.e., match) a predefined viewer expression, the electronic device 102 identifies a portion of the media content item corresponding in time to the viewer expression. For example, upon detecting that a viewer is shocked after watching a shooting scene in a Law and Order episode, the electronic device 102 captures or stores the shooting scene, e.g., as a MPEG file.

In some implementations, when the captured viewer expression does ("Yes"; 508) correspond to (i.e., match) a predefined viewer expression, the electronic device 102 also captures (512) the viewer expression in a second media content item. For example, upon detecting that a viewer is shocked after watching a shooting scene, the electronic device 102 not only stores the shooting scene (from the TV episode), but also stores the viewer's shocked face (captured using the camera 114), and associates the shooting scene with the image including the viewer's shocked face, e.g., using a viewer expression and media content pair 242 (FIGS. 3 and 4).

In some implementations, in response to a user request, the electronic device 102 edits (514) the second media content item to include the captured viewer expression or a reference thereto. For example, when a viewer expression is captured in high resolution (e.g., using a 24 megapixel SLR camera), when a file including the viewer expression exceeds a predefined size (e.g., larger than 8 MB), or when the file including the viewer expression is stored remotely (e.g., on a device other than the electronic device 102), a Google TV device creates a reference or a pointer (e.g., a URL, or a directory path name) to the file including the captured viewer expression in a local file.

In some implementations, the electronic device 102 then transmits (516) information (e.g., a URL or a directory path name) identifying the portion of the media content item to a server. For example, after verifying that a user has appropriate copyright and other required permissions, upon the user's request, a Google TV device uploads a portion of a home-made video at which the user laughed or cried while watching, to the YOUTUBE.com or to the FACEBOOK.com, for sharing with the user's friends or other contacts.

In some implementations, the social network server 110 or the media content server 112 stores (518) the information identifying the portion of the media content item, e.g., for analyzing viewer preference and/or viewing history.

In some implementations, with appropriate copyright permissions, the electronic device 102 uploads (520) the portion of the media content item to a server (e.g., media content server 112). For example, after verifying (e.g., via a copyright verification server remote from the electronic device, or software module resident on the electronic device) that a home-made video is free of copyright claims (for example, in conjunction with a media content server 112 or other Internet-connected copyright licensing resource), the electronic device 102, upon a user's request, uploads the home-made vide, or a portion thereof, to a content sharing website, such as the YOUTUBE.COM website, for sharing with other users. In some implementations, upon receiving the portion of the media content item uploaded and verifying copyright permissions, the media content server 112, e.g., a YOUTUBE server, shares (522) the portion of the media content item (e.g., the home-made video) with the user's social network friends or professional network contacts.

In some implementations, the electronic device 102 transmits (524) information identifying the viewer expression to a server, e.g., for data mining purpose. In some implementations, information identifying a viewer expression includes: what type a view expression is (e.g., crying, laughing, or giggling), when the viewer expression is captured (e.g., on Friday nights, on weekday mornings, or during weekends), how many users are captured in a single expression file (e.g., both Tom and Jerry are captured as shocked in a same photo).

In some implementations, the media content server 112 stores (526) the information identifying the viewer expression. In some implementations, the information is aggregated and analyzed to predict a user's viewing preference. For example, if in the past three month, a server has only received shocked face expressions from user Tom, it can be predicted that the user Tom favors horror or suspense movies to other types of movie.

Figure 6A:
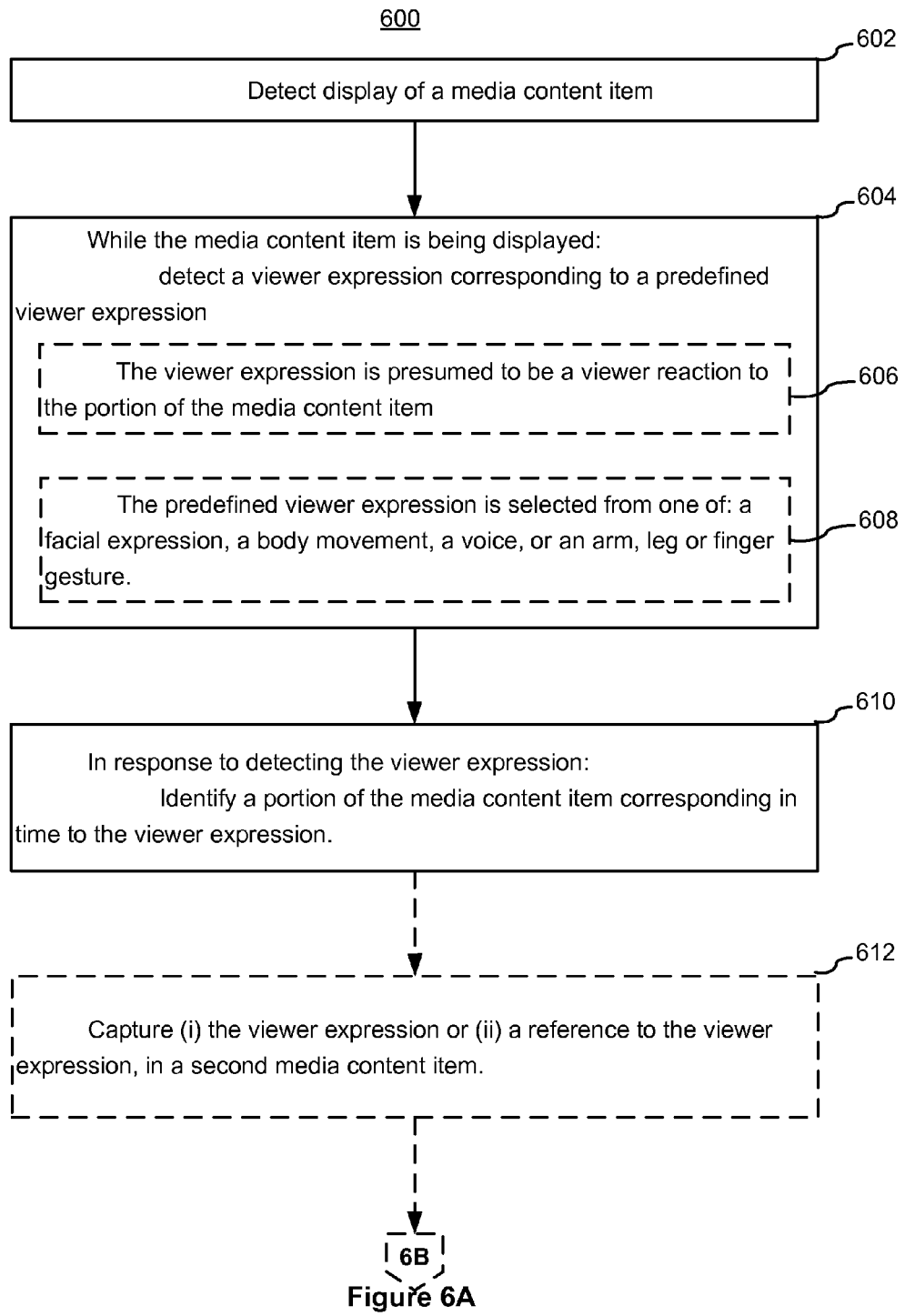
FIGS. 6A-6B are flow charts illustrating a method for capturing media content in accordance with a viewer expression at a computer system in accordance with some implementations.
Figure 6B:
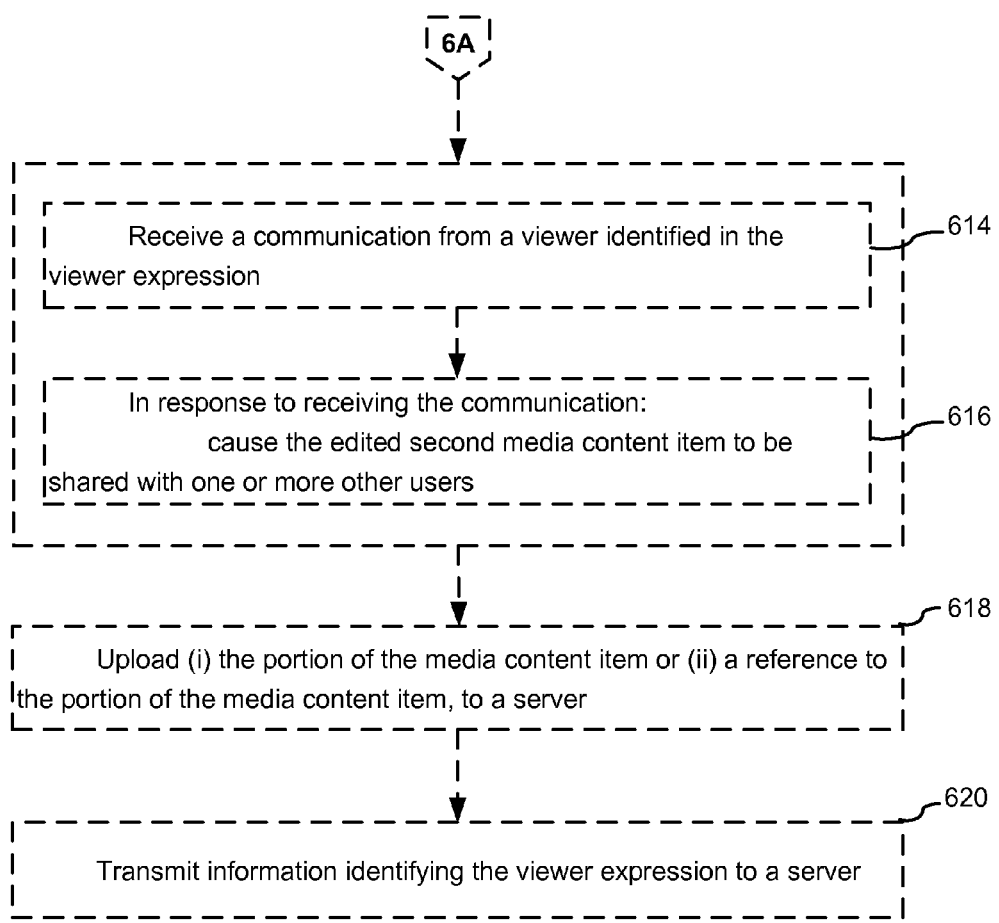

FIGS. 6A-6B are example flow charts illustrating methods 600 for capturing media content in accordance with a viewer expression, e.g., implemented at the computer system 100, in accordance with some implementations.

In some implementations, an electronic device 102 (e.g., a Google TV device, a set-top box, or a TV) detects (602) display of a media content item. For example, a Google TV device checks, periodically on a predefined schedule or randomly, media content (e.g., a TV episode, a movie, a YOUTUBE clip, a sound clip, a web page, and a document) being displayed on a display device, e.g., a TV screen.

In some implementations, while the media content item is being displayed (e.g., while the TV episode is still being displayed or while a song is still being played, or stated in another way, when a viewer is still viewing the TV episode or listening to the song); the electronic device 102 detects (604) a viewer expression corresponding to a predefined viewer expression. For example, a Google TV device first captures a photo or a video clip of a viewer's movements (e.g., rolling eyes, stretching arms or legs, nodding or shaking head), and then compares (using image or video frame comparison techniques) the captured photo or video frames, with photos or video frames known or confirmed to include certain type(s) of viewer expressions, to determine whether the captured photo/video clip includes a particular type of viewer expression, such as a viewer's smiling face or a viewer who appears bored by stretching arms and legs or not looking directly at the TV (on which the TV episode is being displayed). In some implementations, the viewer expression captured includes continuous movements of a viewer, e.g., pacing back and forth, shaking head repeatedly, numerous head movements. In some implementations, the viewer expression captured includes a viewer's facial impression (e.g., a smiling face or rolling eyes), which is presumed to be an accurate prediction of the viewer's reaction to a media content item. In some implementations, a viewer expression also includes bodily movement (e.g., stretching an arm/leg, and nodding or shaking head).

In some implementations, the predefined viewer expression (to which a captured viewer expression is compared) is selected (608) from one of: a facial expression, a body movement, a voice, or an arm, leg or finger gesture. In some implementations, a predefined viewer expression includes different types of body movement (raising an arm/leg, standing up/sitting down, shaking/nodding head, looking straight at or sideways from a TV, a smiling face, a laugh or chuckle, a cry, and facial expressions showing that a viewer is a scared, shocked, despondent, engaged, disengaged, and distracted.

In some implementations, in response to detecting (604) the viewer expression, the electronic device identifies (610) a portion of the media content item corresponding in time to the viewer expression (e.g., one or more viewer expressions {e.g., expression occurrence corresponding to playback position, a time window} (e.g., capturing a 5 second clip of a TV or movie episode)

In some implementations, because (1) a viewer expression is captured while a media content item is still being displayed or (2) the captured expression corresponds in time to (e.g., simultaneously or concurrently with, or within a threshold delay from) the media content item being displayed, the captured viewer expression is presumed (606) to be a viewer's reaction to a portion of the media content item (the viewer is/was watching). For example, a facial expression (e.g., captured by the camera 114) showing that a viewer is shocked is presumable to be the viewer's reaction to watching a gruesome killing scene 3 seconds ago (as opposed to what is currently on display), e.g., due to delay arising from comparing a captured viewer expression with predefined viewer expressions. When the viewer expression is captured or detected, with explicit user consent, to protect user privacy and to comply with relevant privacy laws or contract provisions.

In some implementations, the portion of the media content (e.g., captured by the camera 114 or by the microphone 116) is one of: a video or audio clip, a text (e.g., from a web page or a WORD document at which a viewer was reviewing or reading), or a photo (e.g., an image).

In some implementations, the electronic device 102 captures (612) (i) the viewer expression or (ii) a reference to the viewer expression, in a second media content item. For example, after capturing a viewer's facial expression, a Google TV device stores the viewer expression in a file (e.g., an audio/video clip). For another example, after capturing a viewer's facial expression, a Google TV device stores a reference (such as a URL or a directory path) to the viewer expression in a file (e.g., a log file, a spreadsheet, and an RSS stream) for ease of future reference or for ease of sharing among several users.

In some implementations, the electronic device 102 receives (614) a communication from a viewer identified in the viewer expression (e.g., a user selection of a "share" button to affirmatively indicate the user's intention to share a captured viewer expression with one or more other users); and in response to receiving the communication (e.g., the user selection of the "share" button), the electronic device shares or causes (616) to be shared the edited second media content item (e.g., the audio/video clip including the viewer expression) with one or more other users, e.g., the viewer's friends or contacts on the GOOGLE+CIRCLE network or GOOGLE HANGOUT.

In some implementations, upon obtaining a user request, the electronic device 102 uploads (620) the portion of the media content item (e.g., a 5 second clip of a Law and Order episode) or a reference there to, to a server e.g., for sharing, for storage, for bookkeeping, and for analysis. For example, after a user request for an upload, a Google TV device or its software components cause to be transmitted to a server (e.g., the media content server 112 or the social network server 110) a URL (e.g., "www.nbc.com/48 hours/LawOrder episode_5_Second_Clip") at which the 5 second Law and Order clip can be accessed, such that the URL can be shared with (e.g., accessed by) other users.

In some implementations, information identifying a media content item (e.g., the name of a TV episode), a channel number, and one or more names of cast members) the media content item or a portion thereof (instead of the portion of the media content item itself, which could be of a relatively large size) is uploaded to a server. In some implementations, information identifying the portion of the media content item includes: a channel number, a name of a TV or movie episode, a TV program identifier.

In some implementations, after receiving the information identifying a media content item (e.g., names of different TV episodes a viewer has watched in the past three months), the server collects and analyzes the information to predict user preferences (e.g., viewing preference, such as whether a user prefers action movies to romance movies, or whether a user would rather paying for an ad-free movie than watching advertising or promotional materials in order to gain free access), and to form a user profile (e.g., predicting a user's location, education level, or income level, based on what TV or movie episodes the user has watched in the past three years).

In some implementations, the electronic device 102 transmits (620) information identifying a captured viewer expression to a server, e.g., for sharing with other users. In some implementations, information identifying a viewer expression includes an indication of the category or type to which the viewer expression belongs (e.g., crying, laughing, giggling), when the viewer expression is captured (e.g., on a Friday night, on a weekday morning, or during a weekend), how many users are captured in a single expression file (e.g., both Tom and Jerry are captured as shocked in a same photo). In some implementations, the information is aggregated and analyzed to predict a user's viewing preference. For example, if in the past three months, a server has received more than 90 laughing-face expressions from user Tom, it can be predicted that the user Tom favors comedy movie to horror or suspense movies.

Figure 7:
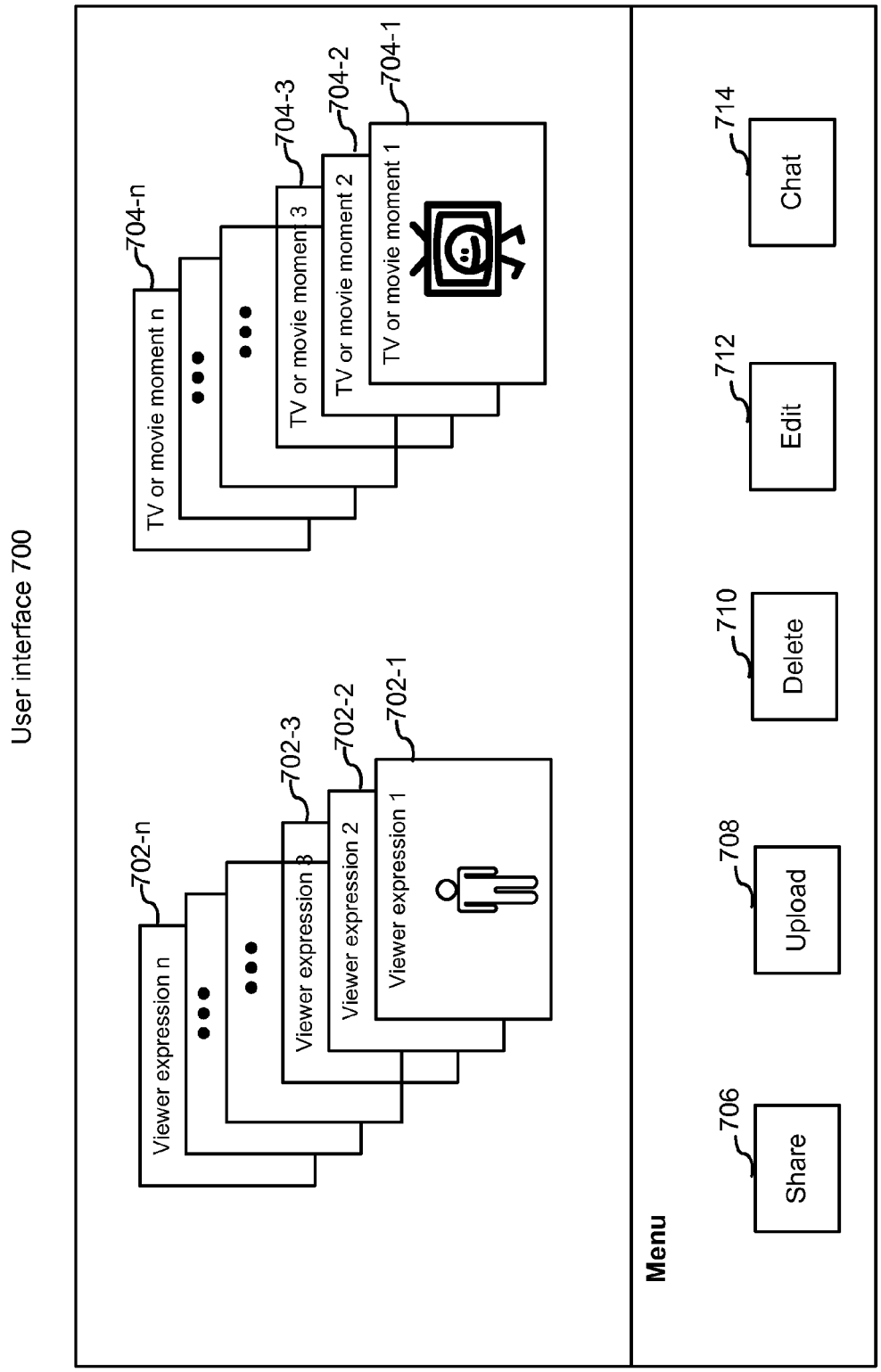
FIG. 7 is a screen image showing an example user interface in accordance with some implementations.

FIG. 7 is a screen image showing an example user interface 700 of a content editing application, in accordance with some implementations. In the user interface 700, one or more viewer expressions (e.g., viewer expression 702-1 . . . viewer expression 702-n) and corresponding TV or movie moments (e.g., TV and movie moment 704-1 . . . TV and movie moment 704-n) are captured and displayed in a content editing application. (I) Captured viewer expressions and (II) corresponding TV or movie moments are shown by way of media content item and viewer expression pairs. For example, the viewer expression 702-1 is shown adjacent to the TV or movie moment 704-1 (to which the viewer expression 702-1 corresponds in time or is presumed to be a reaction). The user interface 700 also includes several menu items, such as share 706, upload 708, delete 710, edit 712, and chat 714. The menu items enable a viewer to share, edits, and communicate with other users, a captured viewer expression and/or a corresponding TV or movie moment (with appropriate copyright permissions).

Figure 8:
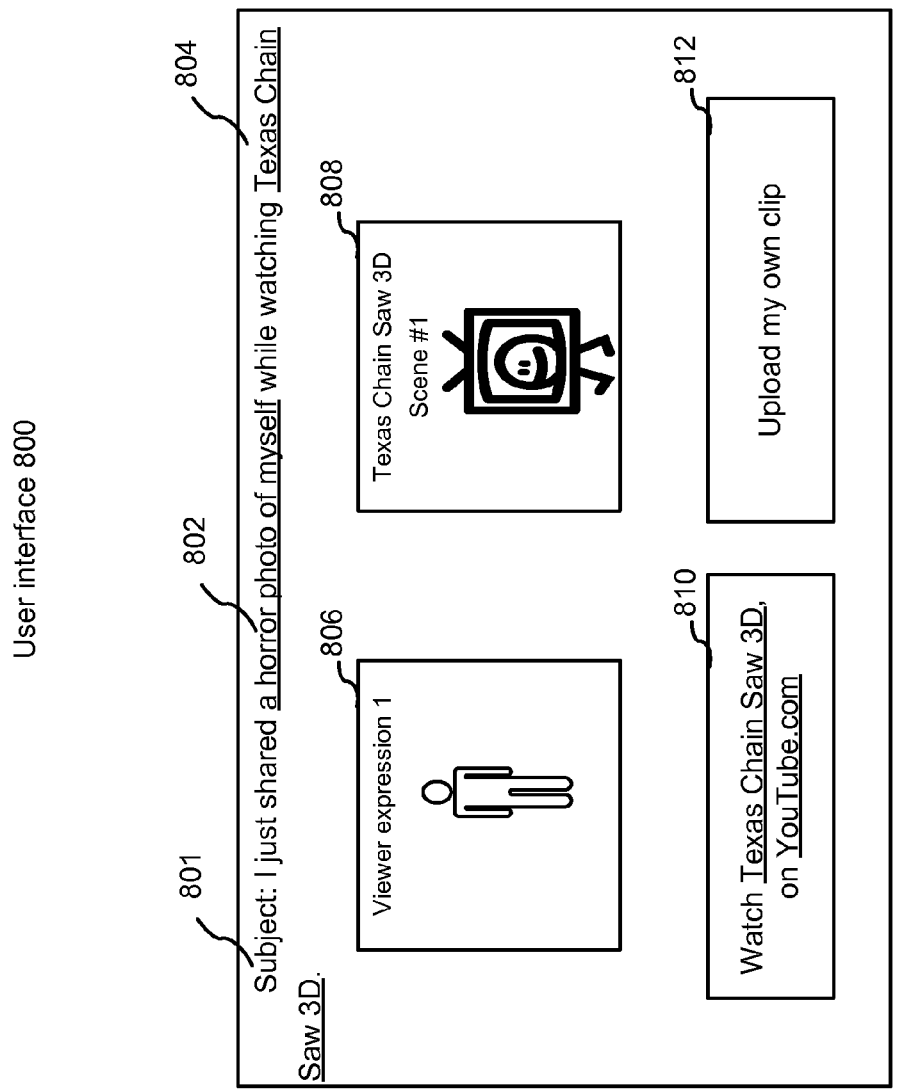
FIG. 8 is a screen image showing an example user interface in accordance with some implementations.

FIG. 8 is a screen image showing an example user interface 800 of a content sharing application, in accordance with some implementations. In the user interface 800, a message (e.g., email or instant messaging) is prepared for a viewer to share captured viewer expressions and TV and movie moments.

As shown in FIG. 8, in some cases, a portion (e.g., the subject line and/or content of) of the message is automatically populated with (e.g., without requiring a user to enter) information gathered from the expression processing module 216 and/or from the comparison module 218. For example, the subject line 801 is automatically populated with (i) information indicating the type of a captured viewer expression (e.g., "a horror photo of myself"), and (ii) information identifying the media content item being displayed (e.g., the "Texas Chain Saw 3D"). As shown, the message also includes a media content item and viewer expression pair, e.g., the viewer expression 806 and scene #1 from the Texas Chain Saw 3D 808.

A link to access (e.g., for free or with payment) the content media item (e.g., the Texas Chain Saw 3D) from a selected (e.g., preferred) content provider (e.g., the YOU-TUBE.COM) is also provided. Another link 812 enabling a viewer to upload his/her own audio/video clips is also provided.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first media content item could be termed a second media content item, and, similarly, a second media content item could be termed a first media content item, which changing the meaning of the description, so long as all occurrences of the "first media content item" are renamed consistently and all occurrences of the "second media content item" are renamed consistently. The first media content item, and the second media content item are both media content items, but they are not the same media content item.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method comprising:
at a computer system having one or more processors and memory storing one or more programs for execution by the one or more processors:
while a media content item is being presented to a user, capturing a momentary reaction of the user to a portion of the media content item;
comparing the captured user reaction with one or more previously captured reactions of the user, wherein each previously captured reaction of the one or more previously captured reactions corresponds to a particular reaction type of a plurality of reaction types; and
identifying the user reaction as one of the plurality of reaction types based on the comparison;
in response to identifying the captured user reaction, identifying the portion of the media content item; and
storing, at the computer system, a first association between the identified user reaction and the portion of the media content item.

2. The method of claim 1, further comprising: determining whether the viewer expression is a viewer reaction to the portion of the media content item.

3. The method of claim 1, further comprising:
capturing (i) the viewer expression or (ii) a reference to the viewer expression, in a second media content item.

4. The method of claim 3, further comprising:
receiving a communication from a viewer identified in the viewer expression; and
in response to receiving the communication:
causing the second media content item to be shared with one or more other users.

5. The method of claim 1, wherein the predefined viewer expression is selected from one of: a facial expression, a body movement, a voice, or an arm, leg or finger gesture.

6. The method of claim 1, wherein the portion of the media content is one of:
a video or audio clip, a text, or a photo.

7. The method of claim 1, further comprising:
uploading (i) the portion of the media content item or (ii) a reference to the portion of the media content item, to a server.

8. The method of claim 1, further comprising:
transmitting information identifying the viewer expression to a server.

9. The method of claim 1, further comprising:
storing the identified viewer expression and the identified portion of the media content item corresponding to the identified viewer expression as a pair.

10. The method of claim 1, further comprising aggregating a plurality of stored associations of the viewer, including the first association, to determine a user viewing preference.

11. The method of claim 1, further comprising, prior to capturing the momentary reaction of the user to the portion of the media content item:
obtaining a prior user reaction of the user;
presenting the prior user reaction to the user;
receiving characterization of the user reaction from the user; and
storing the prior user reaction as a previously captured reaction of the one or more previously captured reactions with a corresponding reaction type.

12. A computer system, comprising:
one or more processors;
memory; and
one or more programs, wherein the one or more programs are stored in the memory and configured to be executed by the one or more processors, the one or more programs including instructions for:
while a media content item is being presented to a user, capturing a momentary reaction of the user to a portion of the media content item;
comparing the captured user reaction with one or more previously captured reactions of the user, wherein each previously captured reaction of the one or more previously captured reactions corresponds to a particular reaction type of a plurality of reaction types; and
identifying the user reaction as one of the plurality of reaction types based on the comparison;
in response to identifying the captured user reaction, identifying the portion of the media content item; and
storing, at the computer system, a first association between the identified user reaction and the portion of the media content item.

13. The system of claim 12, wherein the one or more programs further comprise instructions for:
determining whether the viewer expression is a viewer reaction to the portion of the media content item.

14. The system of claim 12, wherein the one or more programs further comprise instructions for:
capturing (i) the viewer expression or (ii) a reference to the viewer expression, in a second media content item.

15. The system of claim 14, wherein the one or more programs further comprise instructions for:
receiving a communication from a viewer identified in the viewer expression; and
in response to receiving the communication:
causing the second media content item to be shared with one or more other users.

16. The system of claim 12, wherein the predefined viewer expression is selected from one of: a facial expression, a body movement, a voice, or an arm, leg or finger gesture.

17. The system of claim 12, wherein the one or more programs further comprise instructions for:
uploading (i) the portion of the media content item or (ii) a reference to the portion of the media content item, to a server.

18. A non-transitory computer readable storage medium storing one or more programs, the one or more programs comprising instructions, which when executed by a computer system with one or more processors, cause the computer system to:
while a media content item is being presented to a user, capture a momentary reaction of the user to a portion of the media content item;
compare the captured user reaction with one or more previously captured reactions of the user, wherein each previously captured reaction of the one or more previously captured reactions corresponds to a particular reaction type of a plurality of reaction types; and
identify the user reaction as one of the plurality of reaction types based on the comparison; in response to identifying the captured user reaction, identify the portion of the media content item; and
store, at the computer system, a first association between the identified user reaction and the portion of the media content item.

19. The non-transitory computer readable storage medium of claim 18, wherein the one or more programs further comprise instructions for:
determining whether the viewer expression is a viewer reaction to the portion of the media content item.

20. The non-transitory computer readable storage medium of claim 18, wherein the one or more programs further comprise instructions for:
capturing (i) the viewer expression or (ii) a reference to the viewer expression, in a second media content item.

21. The non-transitory computer readable storage medium of claim 20, wherein the one or more programs further comprise instructions for:
receiving a communication from a viewer identified in the viewer expression; and
in response to receiving the communication:
causing the second media content item to be shared with one or more other users.

* * * * *